United States Patent [19]

Nafziger et al.

[11] Patent Number: 4,554,378

[45] Date of Patent: Nov. 19, 1985

[54] PROCESS FOR PREPARING POLYAMINES WITH ION EXCHANGE RESIN CATALYSTS

[75] Inventors: John L. Nafziger, Lake Jackson; Laura A. Rader, Clute; Irwin J. Seward, Jr., Lake Jackson, all of Tex.

[73] Assignee: The Dow Chemical Company, Midland, Mich.

[21] Appl. No.: 468,217

[22] Filed: Feb. 22, 1983

[51] Int. Cl.$^4$ ............................................. C07C 87/50
[52] U.S. Cl. ..................................... 564/332; 564/330
[58] Field of Search ............................. 564/330, 332

[56] References Cited

U.S. PATENT DOCUMENTS 4,039,580 8/1977 Frulla et al. .......................... 564/332
4,039,581 8/1977 Frulla et al. .......................... 564/332

FOREIGN PATENT DOCUMENTS 1210872 2/1966 Fed. Rep. of Germany ...... 564/332
1183153 3/1970 United Kingdom ................ 564/333

Primary Examiner—Robert V. Hines
Attorney, Agent, or Firm—Gary C. Cohn

[57] ABSTRACT

Polyamines are prepared from aromatic amines and aliphatic aldehydes or ketones using cationic or acid ion exchange resins as a catalyst in an essentially oxygen-free atmosphere with the aromatic amines being distilled and protected from the atmosphere.

8 Claims, No Drawings

PROCESS FOR PREPARING POLYAMINES WITH ION EXCHANGE RESIN CATALYSTS

BACKGROUND OF THE INVENTION

The present invention concerns the preparation of aromatic polyamines in the presence of ion exchange resins as catalyst.

The technique of using ion exchange resins as catalysts for preparing aromatic polyamines has been disclosed in Canadian Pat. No. 895,915 issued to Kaiser Aluminum and Chemical Corporation and in European Patent Application publication No. 0,000,778 by Bayer AG. Such catalysts are operable over relatively long periods of time in batch operations. Howver, when the processes are modified to employ such ion exchange resin catalysts by conventional means in continuous processes using plug flow type reactors, they tend to lose their reactivity in a relatively short period of time.

The present invention, therefore, describes a process whereby ion exchange resin catalysts can be employed over extended periods of time.

SUMMARY OF THE INVENTION

The present invention concerns a continuous process for preparing aromatic polyamines which process comprises (A) preparing a precondensate by reacting
  (1) distilled, oxygen-free aromatic amines with
  (2) aliphatic aldehydes, aldehyde releasing materials or ketones;
(B) removing a sufficient amount of water from the precondensate resulting from step (A) such that there remains a single phase containing a sufficient quantity of water to maintain moisture in the resin catalyst;
(C) passing said liquid single phase precondensate through at least one plug flow reactor containing at least one strong acid cation exchange resin selected from
  (1) gelatinous ion exchange resins based on styrene-divinylbenzene copolymers containing not more than 2, preferably from about 0.02 to about 2, weight percent divinylbenzene in said copolymer; and
  (2) macroporous ion exchange resins based on styrene-divinyl benzene copolymers containing at least 10, preferably from about 10 to about 20, weight percent divinylbenzene in said copolymer; or
(D) thereafter recovering the resultant aromatic polyamines from the reaction mixture by suitable means; and wherein
  (a) in step (A), the mole ratio of (1) to (2) is from about 2:1 to about 10:1, preferably from about 2.5:1 to about 8:1, most preferably from about 3:1 to about 5:1;
  (b) the temperature employed in step (A) is from about 0° C. to about 120° C., preferably from about 25° C. to about 100° C., most preferably from about 45° C. to about 55° C.;
  (c) the temperature employed in step (C) is from about 35° C. to about 135° C., preferably from about 45° C. to about 70° C., most preferably from about 50° C. to about 60° C.;
  (d) steps (A), (B) and (C) are conducted in an essentially oxygen-free atmosphere; and
  (e) said ion exchange resin employed in step (C) has been preconditioned by flowing therethrough several volumes of a suitable organic solvent or aqueous mixture of such organic solvent to condition the resin so as to prevent channeling and bed separation during operation of the process.

DETAILED DESCRIPTION OF THE INVENTION

Suitable aliphatic aldehyde or aldehyde releasing materials which can be employed herein include, for example, formaldehyde, formalin (aqueous formaldehyde), trioxane, acetaldehyde, paraformaldehyde, mixtures thereof and the like.

Suitable aromatic amines which can be employed herein include, for example, aniline, N-methylaniline, N-ethylaniline, o-toluidine, o-anisidine, 2,3-xylidine, 3,5-xylidine, o-cyclohexylaniline, o-benzylaniline, α-nephathylaniline, methylmercaptoaniline, 2,4-toluenediamine, 2,6-toluenediamine, mixtures thereof and the like.

Suitable gelatinous strong acid ion exchange resins include, for example, styrene-divinylbenzene copolymers containing not greater than 2 weight percent divinylbenzene in the copolymer and which contains sulfonic acid or methylsulfonic acid groups. Particularly suitable such ion exchange resins are commercially available from The Dow Chemical Company as DOWEX 50WX2, DOWEX 50WX2 SB (0.02% DVB), DOWEX 50WX2 w/BaSO$_4$.

Suitable macroporous strong acid ion exchange resins include, for example, styrene-divinylbenzene copolymers containing greater than 10 weight percent divinylbenzene in the copolymer and which contains sulfonic acid or methylsulfonic acid groups. Particularly suitable such ion exchange resins are commercially available from The Dow Chemical Company as DOWEX MSC-1 or DOWEX MSC-1-H; and Rohm & Haas as AMBERLYST 15 or AMBERLYST XN-1010.

Suitable organic solvents or aqueous mixtures of such solvents which can be employed to condition the ion exchange resins prior to contact with the precondensate include, for example, methanol, acetone, MEK, ethanol, propanol, acetonitrile, tetrahydrofuran, dioxane, mixtures thereof and the like.

The present invention is particularly suitable for preparing polyamines of the diphenylmethane series. The polyamines so produced include mixtures of 2,2'-, 2,4'- and 4,4'-diaminodiphenylmethanes and higher condensation products containing from 3 to about 6 aromatic rings. These compounds are useful in preparing polyisocyanates by reaction with phosgene. Such polyisocyanates are useful in the preparation of polyurethanes. The polyamines are also useful as curing agents for epoxy resins. Other uses include reactions with alkylene oxides to form polyhydroxyl-containing compounds which can be reacted with polyisocyanates to form polyurethanes.

In practicing the present invention, it is preferred to employ two different ion exchange resins by contacting the precondensate with the aforementioned gelatinous ion exchange resin at a temperature of from about 35° C. to about 135° C., preferably from about 45° C. to about 70° C., most preferably from about 50° C. to about 60° C., and thereafter contacting the resultant reaction mixture with the aforementioned macroporous ion exchange resin at a temperature of from about 90° C. to about 135° C., preferably from about 100° C. to about 110° C.

In the use of the two different ion exchange resins, a single reactor with two separate beds and contact zones can be employed or two separate reactors with a single ion exchange resin type in each one can be employed.

Since it is imperative, to insure useful lives of the ion exchange resins before regeneration and that the reaction atmosphere be essentially free of oxygen, it is advantageous and preferred to employ, prior to contact with the aforementioned ion exchange resins, a "guard column" containing an ion exchange resin in a amount of 1% to about 10% of the quantity of subsequent quantities of ion exchange resin. It is preferred to employ a gelatinous resin of the styrene-divinylbenzene type wherein the divinylbenzene content is at least about 4 weight percent. Since, in commercial processes, equipment leaks can occur which would permit air which contains oxygen to get into the process stream and/or stored distilled aromatic amine, the guard column being smaller, more easily observed and more susceptible to deactivation, than such contamination can be discovered by discoloration of the resin and contact with the subsequent ion exchange resin can be stopped before detrimental contamination thereof occurs thus preventing the resin from having to be regenerated prematurely. Activated carbon can be employed as a guard column material instead of or in addition to an ion exchange resin.

The following examples are illustrative of the present invention but are not to be construed as to limiting the scope thereof in any manner.

The following materials were employed in the examples.

ION EXCHANGE RESIN A was a gelatinous strong acid ion exchange resin prepared from a styrene-divinylbenzene copolymer containing 4% divinylbenzene by weight and containing sulfonic acid groups.

ION EXCHANGE RESIN B was a gelatinous strong acid ion exchange resin prepared from a styrene-divinylbenzene copolymer containing 2% divinylbenzene by weight and containing sulfonic acid groups.

ION EXCHANGE RESIN C was a macroporous strong acid ion exchange resin prepared from a styrene-divinylbenzene copolymer containing 18% divinylbenzene by weight and containing sulfonic acid groups.

The reactors employed in the examples were constructed of 47 mm diameter glass tubing 119 cm long and equipped with 2 liter expansion chambers at the top, thermowells and valves suitable for sampling resin and/or product up and down the reactor bed and heating tapes and insulation so as to control the temperature isothermally or in zones.

A "guard column" was constructed from glass tubing ~50 mm in diameter and 20 cm long.

Unless otherwise indicated, the polyamine employed in the examples was aniline which had been distilled from zinc dust and kept under a nitrogen atmosphere so as to exclude oxygen.

Unless otherwise indicated, the general procedure followed in all of the examples was to prepare precondensate by continuously pumping to a nitrogen padded CSTR (continuous stirred tank reactor), a stream of 37–39% aqueous formaldehyde and the aforementioned aniline distilled from zinc dust. The thus formed precondensate was then sent through a decanter operating under a nitrogen pad so as to remove the desired quantity of water, then through a "guard column" also operating under a nitrogen pad and then into a reactor system comprising a single or the first of two reactor columns in series containing a bed of ion exchange resin, which reactor columns were operated under a pad of nitrogen. The effluent from the reactor system was then collected and analyzed by gel permeation chromatography and gas chromatography.

EXAMPLE 1

In this example, a "guard column" was filled with 200 ml of water-wet ion exchange resin A. The first reactor was filled with 2000 ml of water-wet ion exchange resin B and the second reactor was filled with 2000 ml of water-wet ion exchange resin C. Prior to contacting with precondensate, each of the ion exchange resins in the "guard column" and the two reactors were freshly regenerated with 10% aqueous sulfuric acid. The meq/ml of acidity for the resins in the "guard column", first reactor and second reactor was 1.8, 1.8 and 1.6–1.7 respectively. Then each of the ion exchange resin beds, the "guard column", first reactor and second reactor were conditioned by passing one liter volumes respectively of deaerated water, and an 85% methanol water solution downward through the beds. Deaeration of the solvent was accomplished by heating it to boiling, then allowing it to cool under a steady nitrogen purge. The operating conditions and results are given in the following Table I.

TABLE I

| DAY[1] | MOLE[2] RATIO | FIRST REACTOR | | | SECOND REACTOR | | |
|---|---|---|---|---|---|---|---|
| | | TEMP °C. | FLOW RATE ml/sec | YIELD[3] TO 2 RING | TEMP °C. | FLOW RATE ml/sec | YIELD[3] TO 2 RING |
| 1 | 5/1 | 65 | 0.0417 | — | 78 | 0.035 | — |
| 7 | 5/1 | 65 | 0.0383 | 96.5 | 78 | 0.035 | 92.5 |
| 8 | 5/1 | 65 | 0.0333 | 87.6 | 78 | 0.035 | 85.4 |
| 13 | 5/1 | 65 | 0.0333 | 79.5 | 78 | 0.0317 | 85.1 |
| 28 | 5/1 | 60 | 0.0333 | 81.9 | 70 | 0.0333 | 67.9 |
| 30 | 5/1 | 60 | 0.0333 | 84.6 | 60 | 0.0333 | 73 |
| 31 | 5/1 | 60 | 0.0333 | 84.9 | 60 | 0.0333 | 74.1 |
| 34 | 5/1 | 60 | 0.0333 | 75.1 | 60 | 0.0333 | 44.7 |
| 35 | 5/1 | 50 | 0.0333 | 81.9 | 60 | 0.0333 | 80.7 |
| 36 | 5/1 | 50 | 0.0283 | 46.8 | 60 | 0.0317 | 53.7 |
| 37 | 5/1 | 50 | 0.0283 | 84 | 60 | 0.0317 | 19 |
| 41 | 5/1 | 50 | 0.0333 | 63.5 | 60 | 0.0333 | — |
| 48 | 5/1 | 70 | 0.0333 | 82.8 | 70 | 0.0333 | 79.6 |
| 49 | 5/1 | 70 | 0.03 | 77.7 | 70 | 0.0367 | 76.8 |
| 50 | 5/1 | 70 | 0.0383 | 80.1 | 70 | 0.045 | 78.1 |
| 55 | 5/1 | 70 | 0.0333 | 79 | 70 | 0.0333 | 75.2 |
| 56 | 5/1 | 60 | 0.0333 | 73.5 | 70 | 0.0333 | 67.4 |
| 59 | 5/1 | 60 | 0.0667 | 80.4 | 55 | 0.0667 | 59.5 |
| 63 | 5/1 | 55 | 0.0333 | 62.4 | 55 | 0.0333 | 66.3 |

TABLE I-continued

| DAY[1] | MOLE[2] RATIO | FIRST REACTOR | | | SECOND REACTOR | | |
|---|---|---|---|---|---|---|---|
| | | TEMP °C. | FLOW RATE ml/sec | YIELD[3] TO 2 RING | TEMP °C. | FLOW RATE ml/sec | YIELD[3] TO 2 RING |
| 70 | 5/1 | 50 | 0.0333 | 89.5 | 50 | 0.0333 | — |
| 71 | 5/1 | 50 | 0.0333 | 38.6 | 50 | 0.0333 | 15.2 |
| 72 | 5/1 | 50 | 0.0333 | 33.1 | 50 | 0.0333 | 15.2 |
| 85 | 5/1 | 50 | 0.0333 | 52.9 | 50 | 0.0333 | 57.5 |
| 86 | 5/1 | 50 | 0.0333 | 31.8 | 50 | 0.0333 | — |
| 87 | 4/1 | 50 | 0.025 | 85.3 | 50 | 0.025 | 61.2 |
| 90 | 4/1 | 50 | 0.0333 | 75.4 | 50 | 0.333 | 75.7 |
| 91 | 4/1 | 50 | 0.025 | 65.6 | 50 | 0.025 | 69.6 |
| 93 | 2.8/1 | 50 | 0.0217 | 20.1 | 50 | 0.0283 | 14.1 |
| 94 | 2.8/1 | 50 | 0.03 | 40.5 | 50 | 0.0117 | 57 |
| 97 | 2.8/1 | 45 | 0.03 | 74.2 | 50 | 0.433 | 67 |
| 98 | 2.8/1 | 45 | 0.02 | 69.2 | 60 | 0.0367 | 65.5 |
| 99 | 2.8/1 | 45 | 0.025 | 30.5 | 88 | 0.025 | 53.8 |
| 100 | 2.8/1 | 45 | 0.025 | 77 | 74 | 0.025 | 78.5 |
| 104 | 2.8/1 | 45 | 0.025 | 1.53 | 77 | 0.025 | 70.1 |
| 105 | 2.8/1 | 45 | 0.025 | 1.5 | 77 | 0.025 | 69.8 |
| 107 | 4/1 | 45 | 0.035 | 2.1 | 77 | 0.035 | 47.8 |
| 108 | 4/1 | 50 | 0.0333 | 36.4 | 77 | 0.033 | 63.6 |
| 111 | 4/1 | 50 | 0.04 | 19.7 | 77 | 0.04 | 34.1 |
| 112 | 4/1 | 50 | 0.0133 | 35.2 | 94 | 0.0133 | 56.8 |

FOOTNOTES TO TABLE I
[1] For days 1 through 98, the first and second reactors were operated in parallel. For days 99 through 112, reactors 1 and 2 were operated in series.
[2] Mole ratio of aniline to formaldehyde fed to the precondensate reactor.
[3] % of the precondensate 2-ring reaction products converted to 2-ring polyamines, i.e. 2,2'-diaminodiphenylmethane, 2,4'-diaminodiphenylmethane or 4,4'-diaminodiphenylmethane.

EXAMPLE 2

A jacketed reactor, 23 mm by 100 cm was loaded with 250 ml of water-wet resin beads which had been freshly regenerated with 10% $H_2SO_4$. The resin was of the same type used in the first reactor (resin B) in example 1; also it was conditioned in the same manner with deareated solvents. Batches of feed were prepared by mixing freshly distilled aniline (25 moles) and formaldehyde (5 moles), azeotroping off the water, then back adding 3% water, which was somewhat below saturation. No guard column was used, only care taken to exclude air from the feed until after it was pumped thru the reactor. The reactor was held to 70° C. with a heated glycol bath. Feed was pumped thru at 0.30 ml/min.

Yields to polyamines varied from about 70 to 90% over 52 days of operation. The operation was shut down for 20 days, then restarted. The column was not washed out, nor was feed replaced with pure aniline. On restarting, the yield dropped to 50%, then rebounded to the 70's, then lapsed to ~50% on the 20th day after restart. The results are given in Table II.

TABLE II

| Day | Yield |
|---|---|
| 2 | 71.7 |
| 3 | 73.0 |
| 4 | 89.1 |
| 7 | 83.4 |
| 8 | 78.2 |
| 9 | 81.3 |
| 10 | 84.8 |
| 13 | 84.5 |
| 14 | 80.2 |
| 15 | 77.6 |
| 16 | 80.6 |
| 17 | 88.2 |
| 20 | 86.9 |
| 21 | 88.3 |
| 22 | 86.1 |
| 27 | 96.1 |
| 28 | 78.2 |
| 29 | 62.0 |
| 35 | 68.9 |
| 38 | 71.1 |
| 42 | 77.0 |
| 43 | 41.1 |
| 45 | 56.3 |
| 48 | 69.0 |
| 52 | 71.6 |
| 20 day break | |
| 53 | 48.5 |
| 54 | 52.5 |
| 57 | 70.2 |
| 58 | 68.5 |
| 59 | 78.8 |
| 60 | 71.8 |
| 61 | 69.9 |
| 64 | 75.1 |
| 67 | 79.0 |
| 72 | 50.0 |

EXAMPLE 3

A reactor similar to that used in example 2, except shortened to about 65 cm was filled with about 250 ml of water-wet macroporous resin of the type used in the second reactor (ion exchange resin C) of Example 1. The resin was deareated again as per Examples 1 and 2. Heat for this reactor was supplied by an electrical heating tape. Feed was taken from the effluent of the reactor in example 2, starting the 24th day. The reason for this run was to illustrate the use of a second reactor. The temperature was held to 95° C. for the first 17 days, then 100° C. for 7 days, and finally to 105° C. for the remaining 24 days of run time. The results are provided in Table III.

TABLE III

| Day | Temp. | Yield |
|---|---|---|
| 5 | 95° | 93.5 |
| 11 | 95° | 93.8 |
| 14 | 95° | 96.1 |
| 18 | 95° | 97.2 |

TABLE III-continued

| Day | Temp. | Yield |
|---|---|---|
| 19 | 100° | 97.2 |
| 21 | 100° | 95.5 |
| 24 | 105° | 98.1 |
| 28 | 105° | 97.4 |
| 20 day break | | |
| 29 | 105° | 98.2 |
| 30 | 105° | 97.6 |
| 33 | 105° | 97.6 |
| 34 | 105° | 97.4 |
| 35 | 105° | 97.8 |
| 36 | 105° | 97.7 |
| 37 | 105° | 98.4 |
| 40 | 105° | 98.4 |
| 43 | 105° | 97.4 |
| 48 | 105° | 97.4 |

EXAMPLE 4

Three 200 ml columns in parallel were half-filled with test materials: (a) 13 Å molecular sieves, (b) activated carbon (Witcarb 940), and (c) glass beads as a control. The test materials were covered with 1 cm of glass wool, then 100 ml of Resin A was added as an indicator. The columns were heated to 50° C. and precondensate was pumped through each column at 2 ml/min (0.033 ml/sec). Resin A was monitored for darkening at the glass wool interface.

The control showed definite darkening in 32 hours (115,200 s). The column using molecular sieves, showed darkening in less than one hour. The column using activated carbon showed no discoloration after 260 hours (936,000 s) where upon the experiment was discontinued.

EXAMPLE 5 (Comparative)

A set of four 400 ml reactors as described in example 2 were filled with 250 ml of ion exchange resin B. These resin beds were not purged oxygen free. They were washed with (a) 10% $H_2SO_4$, followed by (b) water to neutral effluence as indicated by bromocresol green, (c) absolute methanol, (4 volumes) and (d) aniline which had been distilled, but not rigorously protected from air. The reactors were heated to 70° C. and fed at 0.40 ml/min (0.0067 ml/s) (a) dry distilled aniline, (b) dry distilled aniline saturated with water at ambient temperature (25° C.), (c) 5:1 aniline-formaldehyde feed prepared as in example 2 but without water and with a simple nitrogen pad, and (d) 5:1 aniline-formaldehyde feed as in (c), but with 3% water added, and again, a simple nitrogen pad. The experiment was run only 60 hours (216,000 s). The resin fed only aniline darkened quickly and was black within 24 hours (86,400 s); by 60 hours (216,000 s) these resins were completely opaque. Samples of effluent from the other two reactors were checked for yield; in 26 hours (93,600 s) the reactor fed wet feed was showing about 58% yield while the reactor fed dry feed showed only 35% yield. By 50 hours (180,000 s) the dry system had fallen to less than 1% yield where the wet system had changed little. At 60 hours (216,000 s) the dry system was showing 0.36% yield where the wet system was showing 54% yield to polyamines. The dry system had the bottom quarter blackened and the remainder darkened somewhat; the wet system had only the bottom ⅛ portion of the resin darkened.

EXAMPLE 6 (Comparative)

A set of four 250 ml reactors as described in example 3 were filled with dry resins as follows: (1) and (2) a gel resin 2% crosslinked as in the first reactor in example 1, (3) a gel resin 4% crosslinked as in the "guard column" in example 1, (4) a macroporous resin 18% crosslinked as in the second reactor in example 1. The resins were prepared as follows: (a) all washed with 600 ml 10% $H_2SO_4$, (b) all washed with water to neutral effluence (about 1000 ml), (c) all except reactor (1) washed with absolute methanol, 400 ml, (d) all washed with distilled aniline, sufficient to wet the resins thoroughly. Feed was prepared as in example 2. The reactors were heated to 70° C. and feed was pumped thru at 0.4 ml/min. (0.00667 ml/s) each column. Conversion in all three gel resins was initially about 75-85%, with the 2% not washed with methanol consistently ahead. The macroporous resin started out at 55% conversion; however, the 2% gel resins dropped to about 65% in 8 days, while the macroporous resin improved to 65-70% conversion. The 4% gel resin dropped into the 50's. The feed was replaced with distilled aniline for 5 days (432,000 s), then the experiment was restarted. The 4% crosslinked resin was completely inactive, and had turned quite black at the bottom; the other resins were darkened and showed conversions in the 40-50% range. Further operation showed some improvement; however, the 4% resin remained inactive.

We claim:

1. A process for continuously preparing aromatic polyamines which process comprises
(A) preparing a precondensate by reacting
  (1) distilled oxygen-free aromatic amine with
  (2) aliphatic aldehyde, aldehyde releasing material or ketone;
(B) removing a sufficient amount of water from the precondensate produced in step (A) such that there remains a single phase containing a sufficient quantity of water to maintain moisture in the ion exchange resin catalyst;
(C) passing said liquid single phase precondensate first through a "guard column" and then through at least one plug flow reactor containing at least one strong acid cation exchange resin selected from
  (1) gelatinous ion exchange resins based on styrene-divinylbenzene copolymers containing not more than 2 weight percent divinylbenzene in said copolymer and
  (2) macroporous ion exchange resins based on styrene-divinylbenzene copolymers containing at least 10 weight percent divinylbenzene in said copolymer; and
(D) thereafter recovering the resultant aromatic polyamines from the reaction mixture by suitable means; and
wherein
(a) in step (A), the mole ratio of 1 to 2 is from about 2:1 to about 10:1;
(b) the temperature in step (A) is from about 0° C. to about 120° C.;
(c) the temperature employed in step (C) is from about 35° C. to about 135° C.;
(d) steps (A), (B) and (C) are conducted in an essentially oxygen-free atmosphere;
(e) said ion exchange resin employed in step (C) has been preconditioned by flowing therethrough several volumes of a suitable organic solvent or aqueous mixtures of such solvent to condition the ion exchange resin bed so as to prevent channeling during operation of the process; and (f) said "guard column" contains activated charcoal or an ion exchange resin in an amount of about 1% to about 10% of the volume of ion exchange resin employed in step (C).

2. A process of claim 1 wherein
(a) in step (A), the mole ratio of 1 to 2 is from about 2.5:1 to about 8:1;
(b) the temperature in step (A) is from about 25° C. to about 100° C.;
(c) the temperature employed in step (C) is from about 45° C. to about 70° C.; and
(d) said "guard column" in step (C) contains an ion exchange resin of the gelatinous styrene-divinylbenzene copolymer type containing at least 4% by weight of divinylbenzene in said copolymer.

3. A process of claim 2 wherein
(a) in step (A), the mole ratio of 1 to 2 is from about 3:1 to about 5:1;
(b) the temperature in step (A) is from about 45° C. to about 55° C.;
(c) the temperature employed in step (C) is from about 50° C. to about 60° C.;
(d) The ion exchange resin employed in step (C) has been conditioned with an aqueous solution of methanol containing 80% by weight of methanol; and
(e) said ion exchange resin in step (C) contains sulfonic acid groups or methyl sulfonic acid groups.

4. A process of claims 1, 2 or 3 wherein said precondensate in step (A) is formed from formaldehyde, formalin or a formaldehyde releasing material and aniline.

5. A process of claims 1, 2 and 3 wherein said precondensate in step (A) is formed from formaldehyde, formalin or a formaldehyde releasing material and aniline.

6. A process for continuously preparing aromatic polyamines which process comprises
(A) preparing a precondensate by reacting
(1) distilled oxygen-free aromatic amine with
(2) aliphatic aldehyde, aldehyde releasing material or ketone;
(B) removing a sufficient amount of water from the precondensate produced in step (A) such that there remains a single phase containing a sufficient quantity of water to maintain moisture in the ion exchange resin catalyst;

(C) passing said liquid single phase precondensate through at least one plug flow reactor containing at least one strong acid cation exchange resin selected from
(1) gelatinous ion exchange resins based on styrene-divinylbenzene copolymers containing not more than 2 weight percent divinylbenzene in said copolymer and
(2) macroporous ion exchange resins based on styrene-divinylbenzene copolymers containing at least 10 weight percent divinylbenzene in said copolymer; and
(D) thereafter recovering the resultant aromatic polyamines from the reaction mixture by suitable means; and
wherein
(a) in step (A), the mole ratio of 1 to 2 is from about 2:1 to about 10:1;
(b) the temperature in step (A) is from about 0° C. to about 120° C.;
(c) the temperature employed in step (C) is from about 35° C. to about 135° C.;
(d) steps (A), (B) and (C) are conducted in an essentially oxygen-free atmosphere; and
(e) said ion exchange resin employed in step (C) has been preconditioned by flowing there-through several volumes of a suitable organic solvent or aqueous mixtures of such solvent to condition the ion exchange resin bed so as to prevent channeling during operation of the process.

7. The process of claim 1 wherein said single phase precondensate is sequentially passed through a gelatinous ion exchange resin based on styrene-divinyl benzene copolymer containing not more than 2 weight percent divinylbenzene in said copolymer and then a macroporous ion exchange resin based on styrene-divinylbenzene copolymers containing at least 10 weight percent divinylbenzene in said copolymer.

8. The process of claim 6 wherein said single phase precondensate is sequentially passed through a gelatinous ion exchange resin based on styrene-divinyl benzene copolymer containing not more than 2 weight percent divinylbenzene in said copolymer and then a macroporous ion exchange resin based on styrene divinylbenzene copolymers containing at least 10 weight percent divinylbenzene in said copolymer.

* * * * *